United States Patent [19]
Bourrain et al.

[11] Patent Number: 5,994,374
[45] Date of Patent: Nov. 30, 1999

[54] SUBSTITUTED 1-INDOLYLPROPYL-4-BENZYL-TETRAHYDROPYRIDINE DERIVATIVES

[75] Inventors: Sylvie Bourrain, Harlow; Angus Murray MacLeod, Bishops Stortford; Joseph George Neduvelil, London; Graham Andrew Showell, Bury St. Edmunds, all of United Kingdom

[73] Assignee: Merck Sharp & Dohme Ltd., Hoddesdon, United Kingdom

[21] Appl. No.: 09/068,631

[22] PCT Filed: Nov. 4, 1996

[86] PCT No.: PCT/GB96/02684

§ 371 Date: May 8, 1998

§ 102(e) Date: May 8, 1998

[87] PCT Pub. No.: WO97/17337

PCT Pub. Date: May 15, 1997

[30] Foreign Application Priority Data

Nov. 10, 1995 [GB] United Kingdom .................... 9523064

[51] Int. Cl.⁶ ........................ A61K 31/44; A61K 401/14; A61K 413/14
[52] U.S. Cl. .................. 514/340; 546/271.4; 546/272.4
[58] Field of Search .................. 514/340; 546/271.4, 546/272.4

[56] References Cited

U.S. PATENT DOCUMENTS 5,576,336 11/1996 Baker et al. ............................ 514/323

FOREIGN PATENT DOCUMENTS

94/02477 2/1994 WIPO .
95/32196 11/1995 WIPO .
96/16056 5/1996 WIPO .

OTHER PUBLICATIONS

Cran and Hammond, "Organic Chemistry", Mc–Graw Hill Book Co., NY (1964) 2nd Ed, pp. 565–567.

*Primary Examiner*—Patricia L. Morris
*Attorney, Agent, or Firm*—James L. McGinnis; David L. Rose; Philippe L. Durette

[57] ABSTRACT

A class of 1-[3-(1H-indol-3-yl)propyl]-4-benzyl-1,2,5,6-tetrahydropyridine derivatives, substituted at the 5-position of the indole nucleus by a 1,2,4-triazol-4-yl moiety, and on the methylene linkage of the benzyl moiety by an alkyl, alkoxy, or alkoxy-alkoxy substituent, are selective agonists of 5-HT$_1$-like receptors, being potent agonists of the human 5-HT$_{1D\alpha}$ receptor subtype while possessing at least a 10-fold selective affinity for the 5HT$_{1D\alpha}$ receptor subtype relative to the 5-HT$_{1D\beta}$ subtype. They are therefore useful in the treatment and/or prevention of clinical conditions, in particular migraine and associated disorders, for which a subtype-selective agonist of 5-HT$_{1D\alpha}$ receptors is indicated, and are expected to have fewer undesirable cardiovascular and other side effects.

14 Claims, No Drawings

SUBSTITUTED 1-INDOLYLPROPYL-4-BENZYL-TETRAHYDROPYRIDINE DERIVATIVES

The present invention relates to a class of substituted tetrahydropyridine derivatives which act on 5-hydroxytryptamine (5-HT) receptors, being selective agonists of so-called "5-$HT_1$-like" receptors. They are therefore useful in the treatment of clinical conditions for which a selective agonist of these receptors is indicated.

It has been known for some time that 5-$HT_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-$HT_1$-like or 5-$HT_{1D}$ receptor has recently been shown by molecular cloning techniques to exist in two distinct subtypes. These subtypes have been termed 5-$HT_{1D\alpha}$ (or 5-$HT_{1D-1}$) and 5-$HT_{1D\beta}$ (or 5-$HT_{1D-2}$), and their amino acid sequences are disclosed and claimed in WO-A-91/17174.

The 5-$HT_{1D\alpha}$ receptor subtype in humans is believed to reside on sensory terminals in the dura mater. Stimulation of the 5-$HT_{1D\alpha}$ subtype inhibits the release of inflammatory neuropeptides which are thought to contribute to the headache pain of migraine. The human 5-$HT_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-$HT_{1D}$ agonist sumatriptan (GR43175) to humans is known to give rise at therapeutic doses to certain adverse cardiovascular events (see, for example, F. Willett et al., *Br. Med. J.,* 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-$HT_{1D\alpha}$ and 5-$HT_{1D\beta}$ receptor subtypes (cf. WO-A-91/17174, Table 1), and since it is the blood vessels with which the 5-$HT_{1D\beta}$ subtype is most closely associated, it is believed that the cardiovascular side-effects observed with sumatriptan can be attributed to stimulation of the 5-$HT_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-$HT_{1D\alpha}$ receptor subtype, whilst having a less pronounced action at the 5-$HT_{1D\beta}$ subtype, might be free from, or at any rate less prone to, the undesirable cardiovascular and other side-effects associated with non-subtype-selective 5-$HT_{1D}$ receptor agonists, whilst at the same time maintaining a beneficial level of anti-migraine activity.

The compounds of the present invention, being selective 5-$HT_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-$HT_{1D\alpha}$ receptor subtype. Moreover, the compounds in accordance with this invention have been found to possess at least a 10-fold selective affinity for the 5-$HT_{1D\alpha}$ receptor subtype relative to the 5-$HT_{1D\beta}$ subtype, and they can therefore be expected to manifest fewer side-effects than those associated with non-subtype-selective 5-$HT_{1D}$ receptor agonists.

Several distinct classes of substituted five-membered heteroaromatic compounds are described in published European patent application 0497512, and published International patent applications 93/18029, 94/02477 and 94/03446. The compounds described therein are stated to be agonists of 5-$HT_1$-like receptors, and accordingly to be of particular use in the treatment of migraine and associated conditions. None of these publications, however, discloses nor even suggests the substituted tetrahydropyridine derivatives provided by the present invention.

Moreover, nowhere in the prior art mentioned above is there any disclosure of a subtype-selective 5-$HT_{1D}$ receptor agonist having a 5-$HT_{1D\alpha}$ receptor binding affinity ($IC_{50}$) below 50 nM and at least a 10-fold selective affinity for the 5-$HT_{1D\alpha}$ receptor subtype relative to the 5-$HT_{1D\beta}$ subtype.

The compounds according to the present invention are subtype-selective 5-$HT_{1D}$ receptor agonists having a human 5-$HT_{1D\alpha}$ receptor binding affinity ($IC_{50}$) below 50 nM, typically below 10 nM and preferably below 1 nM; and at least a 10-fold selective affinity, typically at least a 50-fold selective affinity and preferably at least a 100-fold selective affinity, for the human 5-$HT_{1D\alpha}$ receptor subtype relative to the 5-$HT_{1D\beta}$ subtype. Moreover, the compounds in accordance with this invention possess interesting properties in terms of their efficacy and/or bioavailability.

The present invention provides a compound of formula I, or a salt or prodrug thereof:

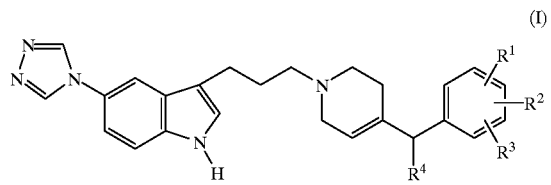

(I)

wherein $R^1$ represents hydrogen, halogen, trifluoromethyl, $C_{1-6}$ alkoxy or a group of formula (a):

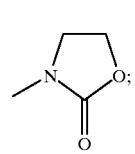

(a)

$R^2$ and $R^3$ independently represent hydrogen, halogen, trifluoromethyl or $C_{1-6}$ alkoxy; and $R^4$ represents $C_{1-6}$ alkyl, $C_{1-6}$ alkoxy or $C_{1-6}$ alkoxy($C_{1-6}$)alkoxy.

The compounds in accordance with the present invention are encompassed within the generic scope of co-pending International Patent Application No. PCT/GB95/01129, published as WO 95/32196 on Nov. 30, 1995. There is, however, no specific disclosure therein of compounds corresponding to those of formula I above wherein $R^1$, $R^2$, $R^3$ and $R^4$ are as defined above.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy" are to be construed accordingly.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

The compounds according to the invention have at least one asymmetric centre, and they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I above, the moiety $R^1$ suitably represents hydrogen, fluoro, trifluoromethyl, methoxy or a group of formula (a) as defined above. Particular values of $R^1$ include hydrogen, fluoro and trifluoromethyl, especially hydrogen or fluoro.

Suitably, $R^2$ and $R^3$ independently represent hydrogen, fluoro, trifluoromethyl or methoxy, in particular hydrogen or fluoro. Suitably, one or both of $R^2$ and $R^3$ represents hydrogen.

Suitably, $R^4$ represents methyl, methoxy, isopropyloxy or methoxyethoxy.

Specific compounds within the scope of the present invention include:
4-(1-phenylethyl)-1-[3-(5-(1,2,4-triazol-4-yl)-1H-indol-3-yl)propyl]-1,2,5,6-tetrahydropyridine;
4-(α-isopropyloxy)phenylmethyl-1-[3-(5-(1,2,4-triazol-4-yl)-1H-indol-3-yl)propyl]-1,2,5,6-tetrahydropyridine;
4-(α-methoxy)phenylmethyl-1-[3-(5-(1,2,4-triazol-4-yl)-1H-indol-3-yl)propyl]-1,2,5,6-tetrahydropyridine;
4-[α-(2-methoxyethyl)oxy]phenylmethyl-1-[3-(5-(1,2,4-triazol-4-yl)-1H-indol-3-yl)propyl]-1,2,5,6-tetrahydropyridine; and salts and prodrugs thereof The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises reacting a compound of formula II with a compound of formula III:

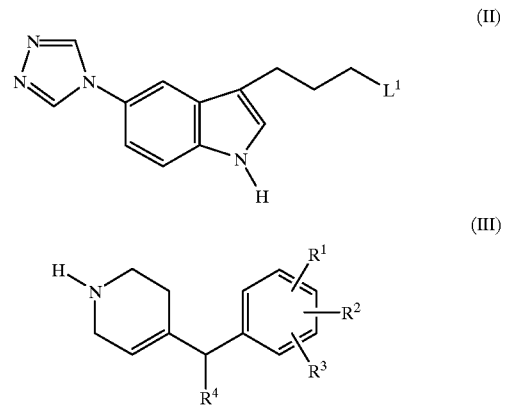

wherein $R^1$, $R^2$, $R^3$ and $R^4$ are as defined above, and $L^1$ represents a suitable leaving group.

The leaving group $L^1$ is suitably an alkylsulphonyloxy or arylsulphonyloxy group, e.g. methanesulphonyloxy (mesyloxy) or p-toluenesulphonyloxy (tosyloxy).

Where $L^1$ represents an alkylsulphonyloxy or arylsulphonyloxy group, the reaction between compounds II and III is conveniently carried out in a suitable solvent such as 1,2-dimethoxyethane or isopropyl alcohol, typically in the presence of a base such as sodium carbonate or potassium carbonate, optionally with the addition of sodium iodide.

In one representative approach, the compounds of formula II wherein $L^1$ represents a mesyloxy or tosyloxy group may be prepared by the sequence of steps illustrated in the following reaction scheme (cf. Larock and Yum, *J. Am. Chem. Soc.*, 1991, 113, 6689):

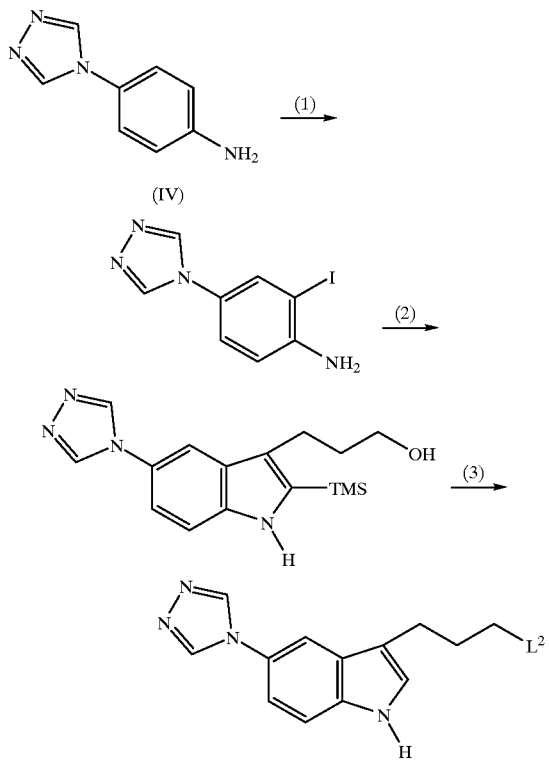

wherein $L^2$ represents mesyloxy or tosyloxy, and TMS is an abbreviation for trimethylsilyl.

In Step 1 of the reaction scheme, the aniline derivative IV is treated with iodine monochloride, advantageously in methanol in the presence of a base such as calcium carbonate, in order to introduce an iodine atom ortho to the amine moiety. Step 2 involves a palladium-mediated coupling reaction with the protected acetylene derivative TMS—C≡C—(CH$_2$)$_3$—OH, typically using palladium acetate and triphenylphosphine in the presence of lithium chloride and sodium carbonate, suitably in N,N-dimethylformamide at an elevated temperature. This is followed in Step 3 by removal of the TMS moiety, ideally in refluxing methanolic hydrochloric acid; followed in turn by mesylation or tosylation, suitably by using mesyl chloride or tosyl chloride respectively in pyridine.

In another representative approach, the compounds of formula II wherein $L^1$ represents a mesyloxy or tosyloxy group may be prepared by reacting 3,4-dihydro-2H-pyran with the compound of formula V:

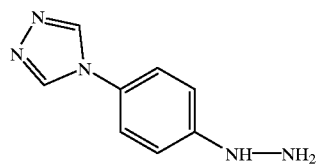

followed by mesylation or tosylation of the 3-hydroxypropyl-indole derivative thereby obtained, typically by treatment with mesyl chloride or tosyl chloride under standard conditions.

The reaction with 3,4-dihydro-2H-pyran is suitably brought about by heating the hydrazine derivative V or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

The hydrazine derivative of formula V above can be prepared by the method described in WO 94/03446, as also can the aniline derivative of formula IV.

Where they are not commercially available, the starting materials of formula III may be prepared by methods analogous to those described in the accompanying Examples, or by standard procedures well known from the art.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-HT$_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-HT$_{1D\alpha}$/5-HT$_{1D\beta}$ Radioligand Binding

Chinese hamster ovary (CHO) clonal cell lines expressing the human 5-HT$_{1D\alpha}$ and 5-HT$_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02-150 nM [$^3$H]-5-HT for saturation studies or 2–5 nM [$^3$H]-5-HT for displacement studies. The final assay volume was 1 ml. 5-HT (10 µM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 µl aliquot of the membrane suspension was incubated, for 10–15 min, in a final volume of 50 µl, at 30° C., with or without forskolin (10 µM), in the presence or absence of test compound. The incubation buffer consisted of 50 mM Tris HCl (pH 7.6 at room temperature), 100 mM NaCl, 30 µM GTP, 50 µM cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 µCi α-[$^{33}$P]-ATP and 1 nCi [$^3$H]-cyclic AMP. The incubation was initiated by the addition of membrane, following a 5 min preincubation at 30° C., and was terminated by the addition of 100 µl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTPγS Binding

Studies were performed essentially as described in *Br. J. Pharmacol.*, 1993, 109, 1120. CHO clonal cell lines expressing the human cloned 5-$HT_{1D\alpha}$ and 5-$HT_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 µg protein/ml for the 5-$HT_{1D\alpha}$ receptor transfected cells and 40–50 µg protein/ml for the 5-$HT_{1D\beta}$ receptor transfected cells. The membrane suspension was then incubated, in a volume of 1 ml, with GDP (100 µM for 5-$HT_{1D\alpha}$ receptor transfected cells, 30 µM for the 5-$HT_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

EXAMPLE 1

4-(1-Phenylethyl)-1-(3-[5-(1,2,4-triazol-4-yl)-1H-indol-3-yl]propyl)-1,2,5,6-tetrahydropyridine Hydrogen Oxalate a) 4-(1-Phenylethenyl)pyridine Methyltriphenylphosphonium iodide (12.13 g, 30 mmol) and potassium t-butoxide (3.37 g, 30 mmol) in anhydrous tetrahydrofuran (110 ml) was stirred and heated at reflux under a nitrogen atmosphere for 1.5 hours. The mixture was cooled to 2° C. then treated with a solution of 4-benzoylpyridine (5.0 g, 27.3 mmol) in anhydrous tetrahydrofuran (30 ml) dropwise. The reaction mixture was stirred at 0° C. for 1 hour then at room temperature for 18 hours. The mixture was treated with saturated ammonium chloride solution (75 ml), the organic layer was collected and the aqueous re-extracted with ethyl acetate (2×100 ml). The combined organics were dried (sodium sulphate), evaporated, then the residue was purified by column chromatography on silica using 25% ethyl acetate in petroleum ether (60–80). The title compound was obtained as a gum (3.77 g, 76%), δ(360 MHz, $CDCl_3$)5.60 (2H, d, J=3 Hz), 7.24–7.40 (7H, m), 8.60 (2H, d, J=5 Hz).

b) 4-(1-Phenylethyl)pyridine

The foregoing olefin (3.75 g, 20.7 mmol) was hydrogenated at 50 psi in ethanol (50 ml) over 10% palladium on carbon. The mixture was filtered and evaporated to give the title compound as a gum (3.28 g, 87%), δ(360 MHz, CDCl$_3$) 1.64 (3H, d, J=7 Hz), 4.11 (1H, q, J=7 Hz), 7.12–7.33 (7.12–7.33 (7H, m), 8.48 (2H, d, J=5 Hz).

c) 1-Benzyl-4-(1-phenylethyl)pyridinium bromide

A solution of the foregoing pyridine (3.25 g, 17.8 mmol) in acetone (25 ml) was treated with benzyl bromide (2.21 ml, 18.6 mmol) and stirred at room temperature for 18 hours. Diethyl ether (25 ml) was-added, the solvent decanted and the precipitate triturated with diethyl ether. The precipitate was collected and dried (6.26 g, 99%), δ(360 MHz, DMSO-d$_6$) 1.67 (3H, d, J=7 Hz), 4.53 (1H, q, J=7 Hz), 5.80 (2H, s), 7.25–7.55 (10H, m), 8.09 (2H, d, J=7 Hz), 9.10 (2H, d, J=7 Hz).

d) 1-Benzyl-4-(1-phenylethyl)-1,2,5,6-tetrahydropyridine

The foregoing quaternary salt (6.20 g, 17.5 mmol) in ethanol (30 ml) and water (5 ml) at 0° C. was treated with sodium borohydride (671 mg, 17.8 mmol). The mixture was allowed to warm to room temperature over 16 hours then treated with a further quantity of sodium borohydride (500 mg, 13.2 mmol). After a further 16 hours the ethanol was evaporated, the residue diluted with water and extracted with ethyl acetate (4×50 ml). The combined organics were dried (sodium sulphate) then evaporated and the residue purified by column chromatography on silica using 25% ethyl acetate in hexane. The title compound was obtained as an oil (3.52 g, 72%), δ(360 MHz, CDCl$_3$) 1.35 (3H, d, J=7 Hz), 1.94–1.98 (2H, m), 2.43–2.55 (2H, m), 3.02–3.10 (2H, m), 3.32 (1H, q, J=7 Hz), 3.59 (2H, s), 5.52 (1H, d, J=2 Hz), 7.15–7.35 (10H, m).

e) 4-(1-Phenylethyl)-1,2,5,6-tetrahydropyridine

A stirred, cooled (0° C.) solution of the foregoing amine (2. g, 7.2 mmol) in anhydrous dichloromethane (30 ml) was treated with α-chloroethyl chloroformate (0.94 ml, 8.7 mmol). The reaction mixture was allowed to warm to room temperature over 16 hours, then evaporated, dissolved in methanol (30 ml) and heated at reflux for 4 hours. The solvent was evaporated, the free base liberated and purified by column chromatography on silica using dichloromethane/methanol/ammonia (9:10:0.1). The title product was obtained as a viscous gum (1.04, 77%), δ(250 MHz, CDCl$_3$) 1.36 (3H, d, J=7 Hz), 1.83–1.88 (2H, m), 2.82–2.93 (2H, m), 3.30 (1H, q, J=7 Hz), 3.37–3.42 (2H, m), 5.59 (1H, d, J=2 Hz), 7.15–7.32 (5H, m). MS, ES$^+$, m/z=188 for (M+H)$^+$.

f) 4-(1-Phenylethyl)-1-(3-[5-(1,2,4-triazol-4-yl)-1H-indol-3-yl]propyl)-1,2,5,6-tetrahydropyridine Hydrogen Oxalate A suspension of 3-(5-[1,2,4-triazol-4-yl]-1H-indol-3-yl)propan-1-ol (220 mg, 0.91 mmol) in anhydrous tetrahydrofuran (30 ml), under an atmosphere of nitrogen, was treated with triethylamine (0.25 ml, 1.82 mmol) and methanesulphonyl chloride (0.14 ml, 1.82 mmol). The reaction mixture was stirred for 1.5 hours, filtered, evaporated then re-dissolved in dichloromethane (50 ml) and washed with water (2×30 ml). The combined organics were dried (sodium sulphate), evaporated and the crude mesylate was suspended in propan-2-ol (50 ml) then treated with potassium carbonate (500 mg, 3.6 mmol) and 4-(1-phenylethyl-1,2,5,6-tetrahydropyridine (482 mg, 2.5 mmol). The reaction mixture was stirred whilst heating at reflux for 66 hours, then cooled and evaporated. The residue was partitioned between water (50 ml) and dichloromethane (50 ml). The aqueous was separated then re-extracted with dichloromethane (3×50 ml). The combined organics were dried (sodium sulphate), evaporated and the residue purified by chromatography on silica using dichloromethane/methanol/ammonia (95:4:1) to give the title compound free base (115 mg, 31%). The hydrogen oxalate salt had mp >120° C. (dec.). MS, ES$^+$, m/z=412 for (M+H)$^+$, δ(360 MHz, DMSO-d$_6$) 1.31 (3H, d, J=7 Hz), 2.02–2.20 (4H, m), 2.78 (2H, t, J=7 Hz), 3.05–3.30 (4H, m), 3.45 (1H, q, J=7 Hz), 3.60–3.80 (2H, m), 5.56 (1H, s), 7.17–7.25 (3H, m), 7.27–7.35 (4H, m), 7.51 (1H, d, J=9 Hz), 7.80 (1H, d, J=2 Hz), 9.01 (2H, s), 11.20 (1H, s). (Found: C, 63,89; H, 6.23; N, 12.24. C$_{26}$H$_{29}$N$_5$·1.45C$_2$H$_2$O$_4$·0.33CH$_3$CH$_2$OH requires C, 63.71; H, 6.13; N, 12.57%).

EXAMPLE 2

4-(α-Isopropyloxy)phenylmethyl-1-(3-[5-(1,2,4-triazol-4-yl)-1H-indol-3-yl]propyl)-1,2,5,6-tetrahydropyridine Hydrogen Oxalate a) α-Phenyl-α-(4-pyridyl)methanol A 1M solution of phenylmagnesium bromide in tetrahydrofuran (100 ml, 100 mmol) was treated with 4-pyridylcarboxaldehyde (10 g, 93.5 mmol) in anhydrous tetrahydrofuran (50 ml) under a nitrogen atmosphere. The mixture was heated at reflux with stirring for 4 hours, cooled to room temperature then treated with saturated ammonium chloride solution followed by dichloromethane then water. The organic layer was separated and the aqueous re-extracted with dichloromethane. The combined organics were dried (sodium sulphate) then evaporated then the residue triturated with hexane/ethyl acetate (3:1) to give the required product (13.5 g, 73%). MS, ES$^+$, m/z=186 for (M+H)$^+$.

b) α-(1-Benzyl-1,2,5,6-tetrahydropyridine-4-yl)-α-phenylmethanol

The foregoing pyridine (10 g, 54 mmol) in acetone (50 ml) was treated with benzyl bromide (6.4 ml, 54 mmol) and the reaction mixture was stirred at room temperature for 18 hours. The oil produced was decanted and triturated with acetone to give the quaternary salt (19 g, 98%). This quaternary salt (12.0 g, 33.7 mmol) in ethanol (500 ml) was treated portionwise with sodium borohydride (1.5 g, 40 mmol). The reaction mixture was stirred at room temperature for 18 hours. The reaction mixture was treated with water, then the majority of the solvent evaporated and the residue extracted into dichloromethane. The organic layer was separated and the aqueous re-extracted with dichloromethane. The combined organics were dried (sodium sulphate) then evaporated and the residue purified by column chromatography on silica using dichloromethane/methanol (9:1) to give the title tetrahydropyridine (7.2 g, 77%), δ(250 MHz, CDCl$_3$) 1.97–2.05 (2H, m), 2.52 (2H, dd, J$_1$=J$_2$=6 Hz), 3.01–3.06 (2H, m), 3.57 (2H, s), 5.10 (1H, s), 5.75–5.79 (1H, m), 7.20–7.3 (10H, m).

c) O-Isopropyl-α-phenyl-α-(1,2,5,6-tetrahydropyridin-4-yl)methanol

The foregoing tetrahydropyridine (2.0 g, 7.1 mmol) in dichloromethane (100 ml), at 0° C., was treated with α-chloroethyl chloroformate (1.7 ml, 16 mmol). The solution was stirred, whilst warming to room temperature, for 18 hours. The solvent was evaporated then the residue treated with propan-2-ol (100 ml) and heated at reflux for 1 hour. The solvent was evaporated and the residue partitioned between saturated aqueous potassium carbonate solution and dichloromethane. The organic layer was separated and the aqueous re-extracted with dichloromethane. The combined organics were dried (sodium sulphate), evaporated then the residue was purified by column chromatography on neutral alumina using dichloromethane/methanol (9:1). The required tetrahydropyridine was obtained as a gum (620 mg, 38%), δ(250 MHz, CDCl$_3$) 1.14 and 1.20 (each 3H, each d, J=6 Hz), 1.90–1.98 (2H, m), 2.92 (2H, dd, J$_1$=J$_2$=6 Hz), 3.39

(2H, d, J=3 Hz), 3.63 (1H, heptet, J=6 Hz), 4.78 (1H, s), 5.70–5.73 (1H, m), 7.23–7.34 (5H, m), MS, ES$^+$, m/z=232 for (M+H)$^+$.

d) 4-(α-Isopropyloxy)phenylmethyl-1-(3-[5-(1,2,4-triazol-4-yl)-1H-indol-3-yl]propyl)-1,2,5,6-tetrahydropyridine Hydrogen Oxalate The title compound free base was obtained (80 mg, 21%) from O-isopropyl-α-phenyl-α-(1,2,5,6-tetrahydropyridin-4-yl)methanol and the mesylate obtained from 3-(5-[1,2,4-triazol-4-yl]-1H-indol-3-yl)propan-1-ol as described in Example 1. The hydrogen oxalate salt has mp >122° C. (dec.). MS, ES$^+$, m/z=456 for (M+H)$^+$, δ(360 MHz, DMSO-d$_6$) 1.07 and 1.13 (each 3H, each d, J=6 Hz), 2.00–2.20 (4H, m), 2.76 (2H, t, J=7 Hz), 3.04–3.35 (4H, m), 3.54 (1H, heptet, J=6 Hz), 3.73 (2H, br s), 4.96 (1H, s), 5.77 (1H, s), 7.26–7.36 (7H, m), 7.50 (1H, d, J=8 Hz), 7.79 (1H, d, J=2 Hz ), 9.01 (2H, s), 11.19 (1H, s). (Found C, 60.80; H, 6.04; N, 11.44. C$_{28}$H$_{33}$N$_5$O. 1.9C$_2$H$_2$O$_4$ requires C, 60.95; H, 5.92; N, 11.18%).

EXAMPLE 3

4-(α-Methoxy)phenylmethyl-1-(3-[5-(1,2,4-triazol-4-yl)-1H-indol-3-yl]propyl)-1,2,5,6-tetrahydropyridine Hydrogen Oxalate a) O-Methyl-α-phenyl-α-(1,2,5,6-tetrahydropyridin-4-yl)methanol α-(1-Benzyl-1,2,5,6-tetrahydropyridin-4-yl)-α-phenylmethanol (7.0 g, 25 mmol) in dichloromethane (200 ml) was cooled to −5° C. then treated with α-chloroethyl chloroformate (6 ml, 55 mmol). The reaction mixture was stirred whilst warming to room temperature over 18 hours. The solvent was evaporated then the residue was dissolved in methanol (200 ml) and heated at reflux for 3 hours. The solvent was evaporated, the free base was liberated and purified by column chromatography on neutral alumina using dichloromethane/methanol (9:1). The title compound was obtained as a gum (2.0 g, 39%). MS, ES$^+$, m/z=204 for (M+H)$^+$, δ(250 MHz, CDCl$_3$) 1.80–1.96 (2H, m), 2.86–2.95 (2H, m), 3.32 (3H, s), 3.37–3.41 (2H, m), 4.54 (2H, s), 5.78–5.84 (1H, m), 7.21–7.40 (5H, m).

b) 4-(α-Methoxy)phenylmethyl-1-(3-[5-(1,2,4-triazol-4-yl)-1H-indol-3-yl]propyl)-1,2,5,6-tetrahydropyridine Hydrogen Oxalate The title compound free base was obtained (150 mg, 30%) from the foregoing tetrahydropyridine and the mesylate obtained from 3-(5-[1,2,4-triazol-4-yl]-1H-indol-3-yl) propan-1-ol as described in Example 1. The hydrogen oxalate salt had mp >90° C. MS, ES$^+$, m/z=428 for (M+H)$^+$. (Found: C, 59.21; H, 5.76; N, 11.68. C$_{26}$H$_{29}$N$_5$O.2C$_2$H$_2$O$_4$ requires C, 59.30; H, 5.47; H, 11.52%).

EXAMPLE 4

4-(α-[2-Methoxyethyl]oxy)phenylmethyl-1-(3-[5-(1,2,4-triazol-4-yl)-1H-indol-3-yl]propyl)-1,2,5,6-tetrahydropyridine Hydrogen Oxalate a) O-(2-Methoxyethyl)-α-phenyl-α-(1,2,5,6-tetrahydropyridin-4-yl)methanol The title compound was obtained (250 mg, 29%) from α-(1-benzyl-1,2,5,6-tetrahydropyridin-4-yl)-α-phenylmethanol using 2-methoxyethanol instead of propan-2-ol, as described in Example 2. MS, ES$^+$, m/z=248 for (M+H)$^+$, δ(250 MHz, CDCl$_3$) 1.73–1.77 (2H, m), 2.90 (2H, dd, J=6 Hz), 3.38–3.42 (5H, m), 3.50–3.62 (4H, m), 4.70 (1H, s), 5.78–5.80 (1H, m), 7.24–7.34 (5H, m).

b) 4-(α-[2-Methoxyethyl]oxy)phenylmethyl-1-(3-[5-(1,2,4-triazol-4-yl)-1H-indol-3-yl]propyl)-1,2,5,6-tetrahydropyridine Hydrogen Oxalate The title compound free base was obtained (100 mg, 26%) from the foregoing tetrahydropyridine and the mesylate obtained from 3-(5-[1,2,4-triazol-4-yl]-1H-indol-3-yl) propan-1-ol as described in Example 1. The hydrogen oxalate salt had mp >109° C. (dec.). MS, ES$^+$, m/z=472 for (M+H)$^+$. (Found: C, 61.00; H, 6.91; N, 11.50. C$_{28}$H$_{33}$N$_5$O$_2$. C$_2$H$_2$O$_4$. 1.5H$_2$O requires C, 61.21; H, 6.51; 11.90%).

What is claimed is:

1. A compound of formula I, or a salt thereof:

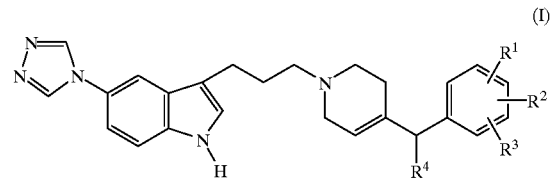

(I)

wherein

R$^1$ represents hydrogen, halogen, trifluoromethyl, C$_{1-6}$ alkoxy or a group of formula (a):

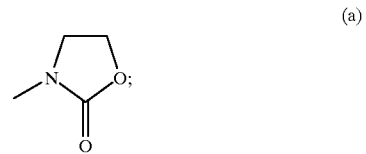

(a)

R$^2$ and R$^3$ independently represent hydrogen, halogen, trifluoromethyl or C$_{1-6}$ alkoxy; and R$^4$ represents C$_{1-6}$ alkyl, C$_{1-6}$ alkoxy or C$_{1-6}$ alkoxy(C$_{1-6}$)alkoxy.

2. A compound as claimed in claim 1 wherein R$^1$ represents hydrogen or fluoro.

3. A compound as claimed in claim 1 wherein R$^2$ and R$^3$ independently represent hydrogen or fluoro.

4. A compound as claimed in claim 1 wherein R$^1$, R$^2$ and R$^3$ each represents hydrogen.

5. A compound as claimed in claim 1 wherein R$^4$ represents methyl, methoxy, isopropyloxy or methoxyethoxy.

6. A compound selected from:
4-(1-phenylethyl)-1-[3-(5-(1,2,4-triazol-4-yl)-1H-indol-3-yl)propyl]-1,2,5,6-tetrahydropyridine;
4-(α-isopropyloxy)phenylmethyl-1-[3-(5-(1,2,4-triazol-4-yl)-1H-indol-3-yl)propyl]-1,2,5,6-tetrahydropyridine;
4-(α-methoxy)phenylmethyl-1-[3-(5-(1,2,4-triazol-4-yl)-1H-indol-3-yl)propyl]-1,2,5,6-tetrahydropyridine;
4-[α-(2-methoxyethyl)oxy]phenylmethyl-1-[3-(5-(1,2,4-triazol-4-yl)-1H-indol-3-yl)propyl]-1,2,5,6-tetrahydropyridine;
or a salt thereof.

7. A pharmaceutical composition comprising an effective amount of a compound of formula I as defined in claim 1 or a pharmaceutically acceptable salt thereof in association with a pharmaceutically acceptable carrier.

8. A method for the treatment and/or prevention of a clinical condition selected from the group consisting of migraine and associated conditions, e.g. cluster headache, chronic paroxysmal hemicrania, headache associated with vascular disorders, tension headache and paediatric migraine, which method comprises administering to a patient in need of such treatment an effective amount of a compound of formula I as defined in claim 1, or a pharmaceutically acceptable salt thereof.

9. A compound as claimed in 2 wherein $R^2$ and $R^3$ independently represent hydrogen or fluoro.

10. A compound as claimed in claim 2 wherein $R^1$, $R^2$ and $R^3$ each represents hydrogen.

11. A compound as claimed in claim 3 wherein $R^1$, $R^2$ and $R^3$ each represents hydrogen.

12. A compound as claimed in claim 2 wherein $R^4$ represents methyl, methoxy, isopropyloxy or methoxyethoxy.

13. A compound as claimed in claim 3 wherein $R^4$ represents methyl, methoxy, isopropyloxy or methoxyethoxy.

14. A compound as claimed in claim 4 wherein $R^4$ represents methyl, methoxy, isopropyloxy or methoxyethoxy.

\* \* \* \* \*